United States Patent [19]

Boucher et al.

[11] Patent Number: 5,443,509
[45] Date of Patent: Aug. 22, 1995

[54] INTERFERENCE BONE-FIXATION SCREW WITH MULTIPLE INTERLEAVED THREADS

[75] Inventors: James A. Boucher; Matthew R. Frushell, both of Clearwater; Niles Mallory, St. Petersburg, all of Fla.

[73] Assignee: Linvatec Corporation, Largo, Fla.

[21] Appl. No.: 988,555

[22] Filed: Dec. 10, 1992

[51] Int. Cl.⁶ .................................. A61F 2/28
[52] U.S. Cl. ........................ 623/16; 606/65; 606/73; 411/412
[58] Field of Search ................ 623/13, 16; 606/65, 606/66, 72, 73, 74; 411/386, 388, 395, 412, 423, 426

[56] References Cited

U.S. PATENT DOCUMENTS

| | | |
|---|---|---|
| 2,242,003 | 5/1941 | Lorenzo . |
| 2,267,925 | 12/1941 | Johnston . |
| 2,570,465 | 10/1951 | Lundholm . |
| 3,541,918 | 11/1970 | Johnson ............... 411/412 |
| 4,463,753 | 8/1984 | Gustilo . |
| 4,537,185 | 8/1985 | Stednitz . |
| 4,576,534 | 3/1986 | Barth et al. ........... 411/412 |
| 4,754,749 | 7/1988 | Tsou . |
| 4,790,850 | 12/1988 | Dunn et al. . |
| 4,861,206 | 8/1989 | Riedel ................... 411/412 |
| 4,870,957 | 10/1989 | Goble et al. . |
| 4,927,421 | 5/1990 | Goble et al. . |
| 4,950,270 | 8/1990 | Bowman et al. . |
| 5,116,337 | 5/1992 | Johnson . |
| 5,120,171 | 6/1992 | Lasner ................... 411/308 |
| 5,139,499 | 8/1992 | Small et al. . |
| 5,139,520 | 8/1992 | Rosenberg . |
| 5,151,104 | 9/1992 | Kenna . |
| 5,152,764 | 10/1992 | Goble . |
| 5,169,400 | 12/1992 | Muhling et al. . |
| 5,188,496 | 2/1993 | Giannuzzi ............... 411/386 |

FOREIGN PATENT DOCUMENTS 8909030 10/1989 WIPO .
9008510 8/1990 WIPO .

*Primary Examiner*—Paul B. Prebilic

[57] ABSTRACT

A bone fixation screw employs plural interleaved and axially symmetrical spiral threads. The threads are machined at the screw tip to form symmetrically disposed leading cutting edges. An interference-screw embodiment has a central axial cannula and a female hexagonal drive socket. The plural threads assist in unbiased starting and fast advance of the screw.

27 Claims, 3 Drawing Sheets

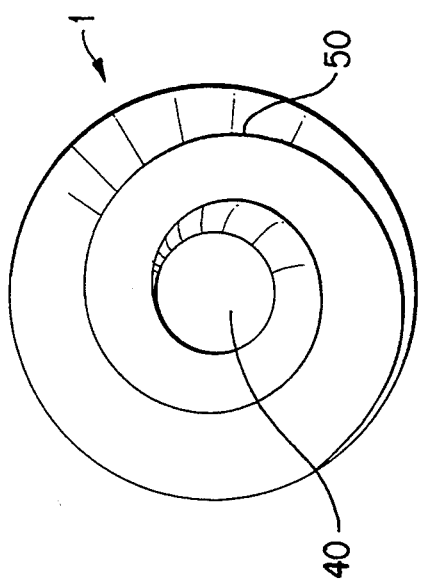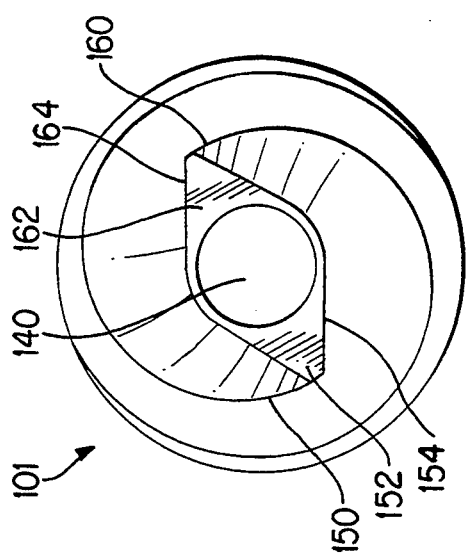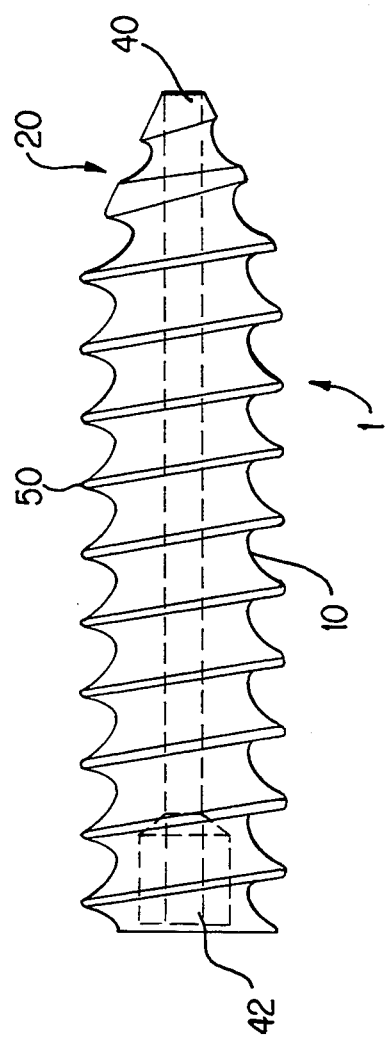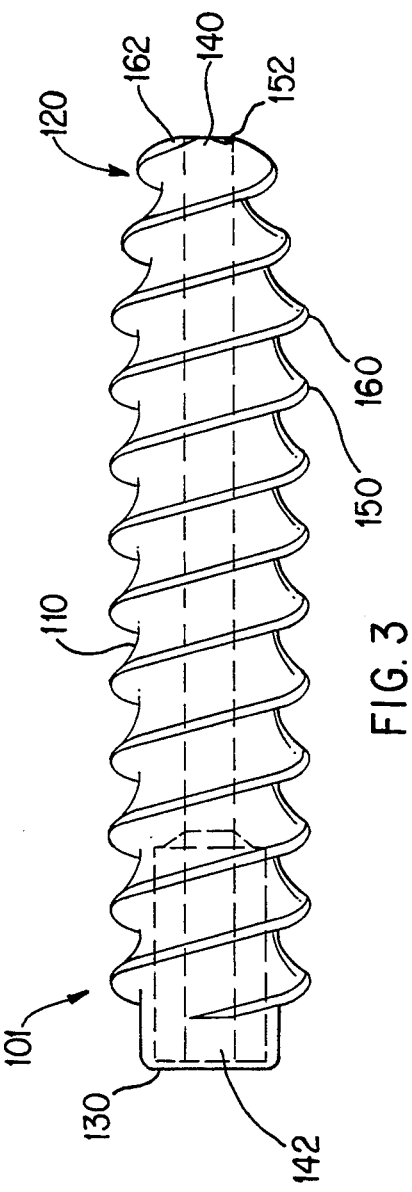

INTERFERENCE BONE-FIXATION SCREW WITH MULTIPLE INTERLEAVED THREADS

BACKGROUND OF THE INVENTION

1. Technical Field

The present invention relates to surgical bone-fixation screws. More specifically, the invention relates to interference screws having particular utility in securing a bone plug in a bone tunnel.

2. Discussion of the Prior Art

Interference screws are used in endoscopic surgery where a bone block, bone plug or plastic substitute therefor is to be fixed in a tunnel or other cavity. This is done, for example, in reconstructing the anterior cruciate ligament of the knee. A procedure for reconstructing this ligament is described in U.S. Pat. No. 5,139,520 (Rosenberg), the entire disclosure from which is incorporated herein by reference. A blind tunnel is drilled into the femur and a ligament is inserted into the tunnel, the inserted end of the ligament terminating in a bone plug. To fix the bone plug (and hence the ligament) inside the femur tunnel, an interference screw is driven into the gap between the tunnel wall and the bone plug. The two pieces of bone do not have sufficient clearance between them to accept the screw; accordingly, as the name implies, the screw creates an interference, and it must force or wedge its way into the gap. Once the interference screw is in place, the plug is firmly held in the tunnel, both by the threads of the screw and by friction due to the large force between the tunnel wall and the adjacent side of the plug opposite the interference screw.

Because they are driven into small spaces that are difficult to observe, interference screws have no head, and are driven by Allen wrenches instead of the Phillips or slot-head screw drivers used for most bone screws. The screw usually includes a central cannula or bore allowing it to be slid over a guide wire, previously fed into the tunnel, to keep the screw on track and aligned. The guide wire is slightly smaller in diameter than the cannula.

An interference screw tends to skew and wander off course, especially when it is starting to progress into hard tissue such as bone. The stiffness of the guide wire reduces this tendency but, since the wire is quite thin (on the order of a millimeter), it tends to bend under strong forces and the screw may wander despite riding on the wire. Interference screws are generally thread-forming screws whose helical threads cut into the bone tissue as they advance. If started at the wrong angle when first driven into hard material, the thread-forming interference screw becomes difficult to realign. Since they are inserted endoscopically into a site of limited accessibility and visibility, interference screws are especially apt to be started askew.

A guide wire passed through a cannulated screw is only one technique for keeping the screw properly aligned; other techniques have been used. An example of another technique is found in U.S. Pat. No. 4,927,421 (Goble et al) disclosing an interference screw with an integral drill bit at its forward end. As the screw is turned, the bit cuts a hole equal in diameter to the minor diameter of the following threads. The bit, having drilled a hole, is held therein and prevented from cocking; the threads follow straight on.

Another technique for minimizing skewing is marketed by Acumed, Inc. under the trade name Oregon Fixation System. In that system an interference screw is provided with a transversely small guide tip projecting forwardly from its distal end to facilitate placement and eliminate the need for guide wires. The root of the screw gradually tapers toward the distal end to permit easier starting and provide more gradual compression.

The Goble et al screw, the Oregon Fixation screw and other interference screws heretofore known in the art employ a single helical thread. The use of one helical thread means that the tip of the screw is asymmetrical, since the single thread must start at one particular angular position at the tip and then helically wind along the shank or body of the interference screw from that point. Lateral force develops on the screw thread when it is driven into hard, resisting tissue such as bone. This force tends to cock the screw and turn it away from its intended path, especially when the screw is first started. With a single thread, the screw tip is usually made cone-shaped to minimize lateral force. (A pointed tip spreads out the lateral forces.) Designs with aggressive cutting action, typically non-conical in shape, are impractical with a single thread.

Another drawback to the single thread is that the screw advances slowly. If a certain number of threads per inch are needed for holding power, the advance is limited to the pitch (distance between threads) in a single turn.

The shallow thread angle of the single-thread screw also requires that a high torque be applied to the screw. With steeper angles, a forward force component parallel to the screw axis helps to drive the screw and reduces the required torque. Reduced torque lessens the chance of stripping the screw-driving socket.

OBJECTS AND SUMMARY OF THE INVENTION

It is therefore a primary object of the present invention to provide a bone-fixation screw with a minimum tendency to become misaligned during insertion, especially when starting.

It is another object to provide a bone-fixation screw requiring less torque to drive and resistive to stripping of the drive socket.

It is yet another object to provide a bone-fixation screw capable of aggressively cutting into bone tissue.

It is a further object to provide a bone-fixation screw with the widest possible latitude in thread design to allow the design to be optimized for use in bone, in other tissues, or in combinations of tissues.

It is a still another object to provide a bone-fixation screw which advances and seats quickly.

In accordance with the present invention, a bone-fixation screw includes plural interleaved helical threads. The threads are evenly spaced and congruently shaped, so that at the forward tip of the screw the threads are angularly spaced evenly and symmetrically about the axis of the screw.

The symmetrical spacing means that all the forces developed at the tip, when cutting and forcing aside the tissues to form threads, are balanced and cancel, leaving only a torque along the axis of the screw. The cancellation of lateral forces on the screw tip prevents cocking, misalignment, cross-threading, and wandering of the screw from its intended course.

The thread pitch, the thread angle, and the axial advance per turn are all proportional to the number of interleaved threads. Plural threads cause the screw to advance more quickly, resulting in faster surgery and quicker embedding of the screw, in turn reducing the chance of cocking. The increased pitch also reduces the amount of torque needed to be applied to the screw, and so reduces the chance of stripping the drive socket.

The above and still further objects, features and advantages of the present invention will become apparent upon consideration of the following detailed description of a specific embodiment thereof, particularly when considered in conjunction with the accompanying drawings wherein like reference numerals in the various figures are utilized to designate like components.

BRIEF DESCRIPTION OF THE DRAWINGS

FIG. 1, labelled "prior art," is a side view in elevation of an interference screw with a single thread.

FIG. 2, labelled "prior art," is a forward end view in elevation of the interference screw of FIG. 1.

FIG. 3 is a side view in elevation of the interference screw of the present invention.

FIG. 4 is a forward end view in elevation of the interference screw of FIG. 4.

DESCRIPTION OF THE PREFERRED EMBODIMENTS

Figure 5:
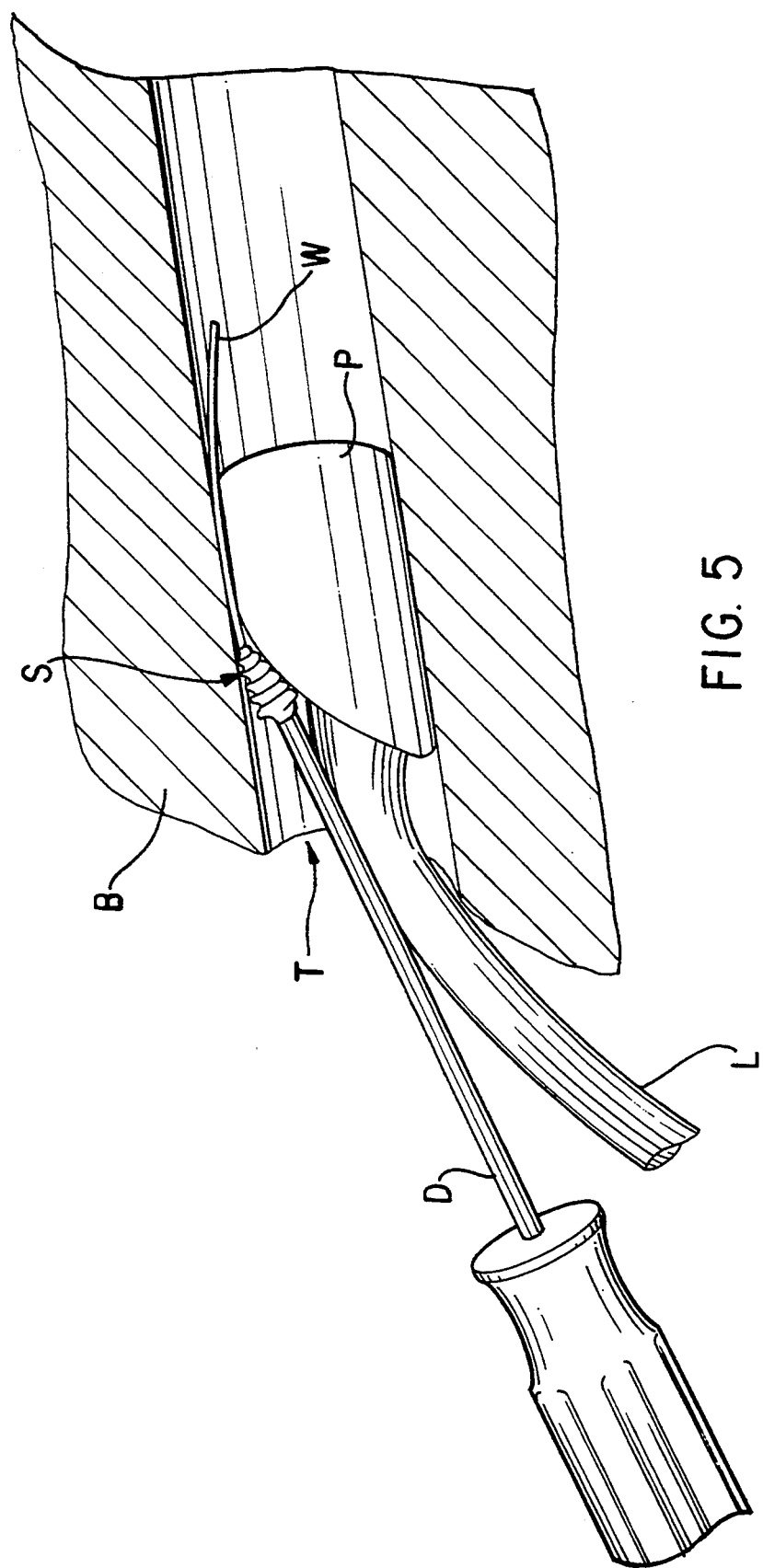
FIG. 5 is a side view in partial section of an interference screw of the present invention being driven between a bone tunnel and a bone plug.

In orthopaedic surgery, bone-fixation screws are used extensively. These screws are of course sterile, and are made from bio-compatible materials. Thread-forming screws, including flutes and sharp thread edges to cut threads as the screw advances, are sometimes used in bone surgery. Interference thread-cutting screws have generally relied upon threads of increasing diameter from a pointed tip to facilitate cutting into and pushing aside the tissues into which the screw thread advances. These screws often use gimlet tips or cone tips. In a gimlet tip, the threads continue from the shank to the tip of the screw, retaining substantial depth until reaching the apex. A surgical screw with a gimlet tip is disclosed in the above-mentioned Rosenberg patent. In a cone tip the threads first appear some distance from the tip point, and the tip itself has a smooth conical or frusto-conical configuration.

FIGS. 1 and 2 of the accompanying drawings illustrate a conventional prior art interference screw 1 combining the gimlet and cone tips. The apex or ridge of the single thread of screw 1 is visible in FIG. 2 as a line spiralling away from a cannula bore 40 toward the ridge of the engaging threads. Specifically, interference screw 1 includes a shank or body 10 with a generally cylindrical outer surface. Around the cylindrical surface of shank 10 there is wound a single helical thread 50. The outer ridge of thread 50 describes a second cylindrical surface, coaxial with the shank surface, constituting the major diameter of the thread. Shank 10 terminates in a generally frusto-conical tip 20 located at the forward end of screw 1. Tip 20 advances when screw 1 is driven counter-clockwise (as viewed in FIG. 2; that is, thread 50 is a normal right-handed thread).

Cannula bore 40 extends coaxially with shank 10 through the entire axial length of screw 1, as indicated by dashed lines. Cannula bore 40 widens at the rear end of shank 10 into a hexagonal socket 42 (also shown by dashed lines). Socket 42 accepts an Allen wrench for driving the screw.

Utilization of an interference screw is illustrated in FIG. 5. Specifically, interference screw S is shown within a drilled bone tunnel T in bone tissue B, about to be driven between and into engagement with the wall of tunnel T and a bone plug P. A ligament L is attached to bone plug P and extends out from tunnel T. Strong muscle tension is typically exerted on ligament L during flexion and extension of the knee so that bone plug P must be secured firmly in tunnel T by interference screw S.

To guide interference screw S into the gap between bone plug P and the wall of tunnel T, a guide wire W is used. Guide wire W is first passed between wall W and plug P, and screw S is then slid along the wire with the wire extending through cannula bore 40. Interference screw S glides closely over wire W to the gap.

A special driver D, having a central longitudinal bore contoured to match cannula bore 40 of screw 1, can be used to drive screw S while wire W remains disposed within the screw cannula bore and the aligned bore of driver D.

The diameter of wire W is smaller than the diameter of cannula bore 40; accordingly, lateral forces exerted on screw S could bend wire W and push the screw S off-course. The only substantial forces present in driving the screw are those exerted by the surgeon. These forces include axial forces directed parallel to wire W since wire W passes axially through screw S and the driver D itself. Axial forces do not cause screw S to become skewed; neither does torque exerted on screw S by the surgeon cause the screw to wander from its path. Rather, the problematic forces exerted on the screw are lateral forces (i.e., forces directed transverse to the screw axis) arising by reaction to the torque exerted on screw S. When the cutting edge of a helical thread pushes against hard bony tissue, the tissue pushes back with a reaction force. If the thread is asymmetrical, the reaction force on the thread is unbalanced, and the resulting lateral force tends to cock screw S out of line.

Referring again to FIGS. 1 and 2, and considering screw 1 of FIGS. 1 and 2 in the position and use of screw S of FIG. 5, it will be seen that the screw diameter at tip 20 of screw 1 is reduced so that the screw can gradually advance into the interference region between the tunnel wall and bone plug by wedging or penetration. Tip 20 is formed into a generally frusto-conical shape to accomplish the wedging action, with the height of thread 50 gradually reduced to zero as the thread spirals toward tip 20 which is smoothly frusto-conical near its apex.

The frusto-conical shape of tip 20 tends to reduce unbalance during insertion somewhat by: first, spreading the cutting reaction force of thread 50 over a long ramp of gradually increasing height; and second, by wrapping the ramp around the screw axis through a large angle. This tendency toward balance, however, is achieved at the sacrifice of cut aggressiveness and rapidity of screw advancement.

The opposite of the conical tip screw would be a single-thread screw with no frusto-conical ramp and with no angular spreading of reaction forces. Such a screw would have a very aggressive cut, and the cutting edge would appear as a straight line perpendicular to the axis in both an end view and a side view of the screw. All of the forces on the cutting edge would be parallel, and all would add to a large single reaction force pushing the screw tip sideways. For a thread-cutting bone fixation screw a short, straight single cutting edge is clearly impractical. The screw would readily become skewed and would be very difficult to start into the bone tissue. Since an aggressive bone-cutting thread cannot be wrapped about a large angle to spread out and cancel the reaction forces, the tip of a single-thread interference screw is limited to either a gimlet, a cone, or some combination of these shapes.

The present invention overcomes the cocking or skewing tendency and design limits of the prior art by the use of plural interleaved threads. FIGS. 3 and 4 illustrate an interference screw 101 configured, in accordance with the principles of the present invention, to have two interleaved threads 150, 160 for fixation use in bone.

The interference screw of the present invention shares many of the features of the prior art interference screw S depicted in FIGS. 1 and 2. Screw 101 includes a generally cylindrical shank (or body) 110, at a forward end of which is a tip portion 120 where threads 150 and 160 terminate at locations disposed symmetrically about the screw axis. The root diameters of the threads taper toward the distal end from a location approximately one-quarter of the length of the screw from that end. A cannula bore 140 runs axially through shank 110. At the rear or proximal end 130 of the screw, cannula 140 expands into a hexagonal socket 142 for accepting an Allen-wrench type driver.

As best shown in FIG. 4, threads 150 and 160 terminate at respective generally planar tip surfaces 152, 162 disposed substantially perpendicular to the longitudinal axis of screw 101. Because threads 150, 160 are symmetrical about the axis of screw 101, tip surfaces 152, 162 are also symmetrical on either side of cannula bore 140. If tip surfaces 152, 162 are coplanar, or in different planes and similarly angled to the axis, or not coplanar but themselves symmetrical (as in a twist drill), then they will be congruent and radially symmetrical if screw 101 is radially symmetrical, as is the case when the plural interleaved threads are similar and equally spaced. (Radial symmetry is characterized by congruent shapes disposed about a central axis and repeating at an angle, where the angle is an integral sub-multiple of 360°. A hexagonal driver or socket has this symmetry, as would any cross-section of a screw with plural, evenly-spaced, interleaved threads.)

The intersections of the generally planar tip surfaces 152, 162 with respective rearward surfaces of threads 150, 160 form respective sharp cutting edges 154, 164. These cutting edges extend outward from the cannula bore in a nearly radial direction, a feature permitting the edges to cut aggressively into bone tissue.

In contrast to the ridge of thread 50 of prior-art screw 1, which (as seen in FIG. 2) spirals smoothly to cannula 40 from the outer periphery of the screw, the ridges of threads 150, 160 do not spiral continuously into cannula bore 140.

Figure 6:
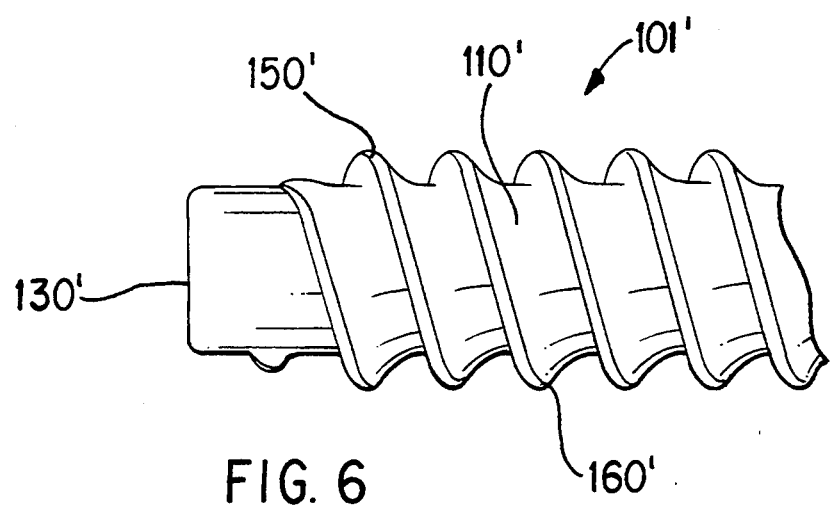
FIG. 6 is a side view in elevation of the proximal end of a first modification of the interference screw of the present invention.

Another interference screw 101' of the present invention is illustrated in FIG. 6 and is characterized by the crest of both of the threads 150' and 160' tapering toward the proximal end 130' of the screw. Specifically, the thread crests taper toward the root diameter of shank 110' to facilitate revision of the screw in a rearward direction. In addition, the outside or cutting edge of threads 150' and 160' become gradually blunter toward proximal end 130'.

Figure 7:
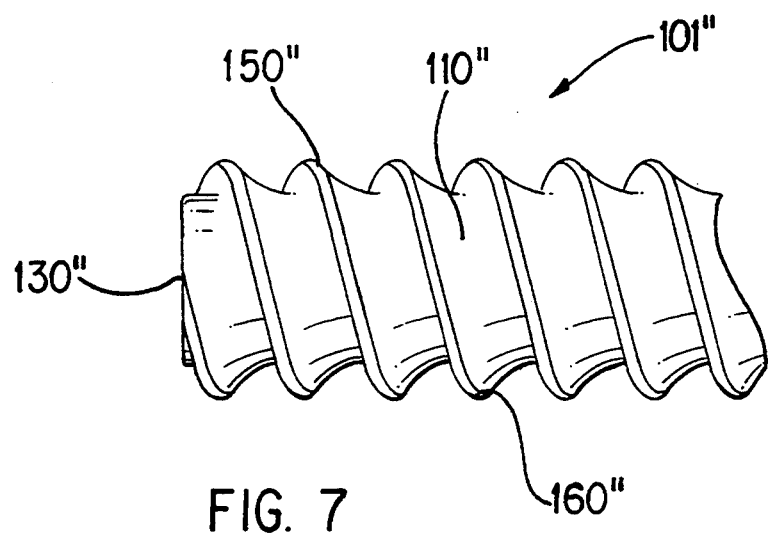
FIG. 7 is a side view in elevation of the proximal end of a second modification of the interference screw of the present invention.

In FIG. 7, screw 101'' is a further embodiment of the invention characterized by the proximal ends of threads 150'' and 160'' terminating in a common plane at the proximal end 130'' of shank 110''. This configuration strengthens the proximal end of the screw because the wall of the shank is thicker about the hexagonal socket.

Figure 8:
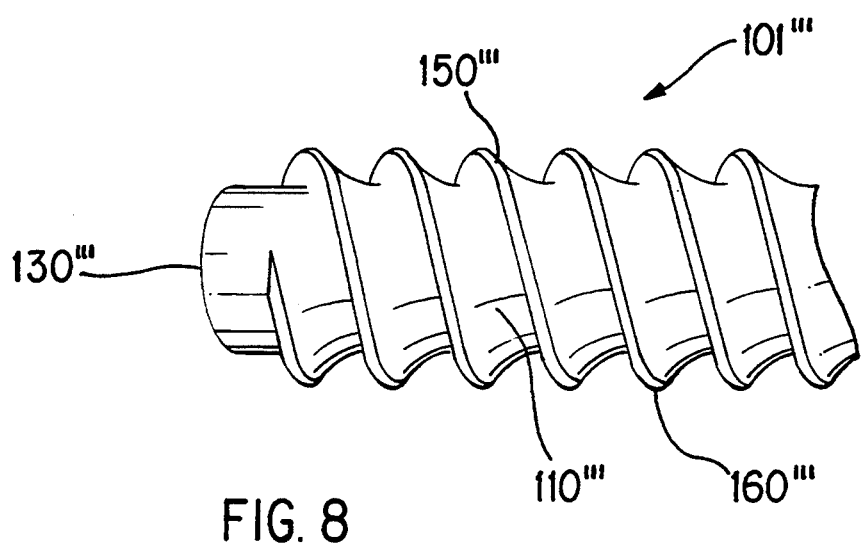
FIG. 8 is a side view in elevation of the proximal end of a third modification of the interference screw of the present invention.

Finally, screw 101''' illustrated in FIG. 8 is characterized by a rounded or radiused proximal end 130''' of shank 110'''. This feature provides a "soft bottom" for the screw to minimize trauma to tissue surrounding the graft during ambulatory activities of the patient.

The advantages of the interleaved bone fixation screw threads of the present invention are numerous:

First, there are no unbalanced lateral or sideways forces on the screw tip to skew it when starting the screw or penetrating hard tissues. The cutting edge of each thread develops the same amount of force, and if the threads are symmetrically disposed, there is no net lateral force. In non-uniform materials, or when the screw enters a uniform material at an angle, one of the threads will bite into the material before the other, and the forces will not be perfectly balanced. However, the imbalance is lessened by the provision of plural threads because there is only a half revolution between "bites".

Second, the lowered risk of skewing or cocking frees the cutting portion of the thread to be as aggressive as desired. Plural threads allow the line of the thread ridge, as seen axially, to assume any shape, thereby permitting greater design choices. The thread shape, the outline of the screw, and other factors can be optimized for use in one tissue or in a combination of tissues. The wide-tipped outline of screw 101, as seen in FIG. 3, would not be feasible without the use of plural threads.

Third, a screw is less likely to wander from the desired insertion direction if the thread is more aggressive, since the screw threads become deeply embedded more quickly.

Fourth, the interleaved threads permit the screw to advance more quickly. With two interleaved threads the pitch is doubled, and likewise the distance the screw advances in one turn; with three threads, the pitch is tripled and likewise the advance.

Fifth, faster advance not only saves time during surgery; it also decreases the risk of the screw mis-threading. A more rapidly advancing screw will more quickly seat itself into the formed threads and will be held more firmly. Screws are most liable to skewing when first started; the more quickly it is embedded, the less likely it is to turn aside from its path.

Sixth, the steep helix angle of plural threads means that the screw is driven more by axial driving force and less by torque than is a single-thread screw. This is so because the threads, in the thread-forming region, everywhere cut into the tissue in a direction lying along the thread ridge. Reduced torque has several advantages: the surgeon can more easily drive the screw by a combination of pushing and turning than by turning only; the risk of stripping the screw socket is decreased; and the screw can be made thinner, and the driver larger.

Seventh, the screw has more engaged thread length for greater holding power, since the tip is wider.

The interleaved thread bone fixation screw is particularly useful in endoscopy where the screw cannot be seen or manipulated directly, and where unbiased starting is most important. However, it is to be understood that the present invention is not restricted to any particular surgical operation, nor for use in pre-drilled holes, nor to interference screws only.

The advantages of plural threads described above increase with multiplication of the thread number, and numbers of interleaved threads greater than two are specifically contemplated by the present invention.

It is to be understood that the terms "fixation" or "fixation-use" as employed herein means attachment to, or a use serving to fixate something in, bone tissue. In this regard, the features of the invention are broadly applicable to interference screws, suture anchors, bone screws, and the like.

Having described a preferred embodiment of a bone-fixation screw in accordance with the present invention, it is believed that other modifications, variations, and changes will be suggested to those skilled in the art in view of the teachings set forth herein. It is therefore to be understood that all such variations, modifications, and changes are believed to fall within the scope of the present invention as defined by the appended claims.

What is claimed is:

1. A bio-compatible screw for fixation-use in bone tissue and adapted to be rotated by a driver, said screw comprising:
    a shank having a longitudinal axis, a distal tip,, and a proximal end;
    plural interleaved helical threads disposed about said shank for engaging the bone tissue;
    driver receiving means at said proximal end for engaging the driver; and
    termination means for minimizing net lateral force exerted on said distal tip during insertion of the screw into bone tissue;
    wherein said termination means comprises plural respective planar tip surfaces of said plural threads at said distal tip at plural respective locations disposed symmetrically about said longitudinal axis.

2. The screw according to claim 1, further including cutting edges formed by intersections of said tip surfaces with respective surfaces of said threads.

3. The screw according to claim 2, wherein said tip surfaces are substantially perpendicular to said longitudinal axis.

4. The screw according to claim 3, wherein said tip surfaces are substantially co-planar.

5. The screw according to claim 1, wherein each of said threads includes a spiral ridge terminating at a location on said distal tip at a radially outermost part of a respective tip surface.

6. The screw according to claim 1, wherein said plural threads are two in number.

7. The screw according to claim 1, further including a cannula bore defined in said shank coaxially with said longitudinal axis and extending entirely through said screw.

8. The screw according to claim 1, wherein said plural threads are disposed at regularly spaced locations along said longitudinal axis.

9. The screw according to claim 1, wherein said threads have respective root diameters that gradually taper toward said distal tip.

10. The screw according to claim 1 wherein said proximal end is radiused.

11. The screw according to claim 1 wherein said threads have respective crests and respective roots, and wherein said crests taper proximally toward said roots at said proximal end.

12. The screw according to claim 11 wherein said threads each have a cutting edge at their crests, said cutting edge becoming gradually blunter toward said proximal end.

13. The screw according to claim 11 wherein said taper of said thread crests extends through said root.

14. A bone fixation screw comprising a shank of bio-compatible material having a longitudinal axis and plural interleaved helical threads extending along its length, said plural threads being disposed symmetrically about said longitudinal axis, wherein said shank has a distal tip with plural planar tip surfaces terminating respective helical threads, said tip surfaces positioned at respective locations disposed symmetrically about said longitudinal axis, each tip surface having leading cutting edge corresponding to an intersection of said tip surface with a respective one of said threads.

15. The bone fixation screw according to claim 14 wherein said plural tip surfaces are substantially coplanar and substantially perpendicular to said longitudinal axis.

16. The bone fixation screw according to claim 14 wherein said plural threads are two in number, and wherein the axial distance between successive longitudinally spaced crests of each individual thread is twice the axial distance between successive longitudinally spaced crests of the interleaved threads.

17. The bone fixation screw according to claim 14 wherein said shank further includes a cannula bore defined entirely through said shank concentrically about said longitudinal axis.

18. A bio-compatible screw for use in bone tissue and adapted to be rotated by a driver, said screw comprising:
    a shank having a longitudinal axis, a distal tip and a proximal end;
    at least one helical thread disposed about said shank for engaging bone tissue, said thread having a crest and a root; and
    driver receiving means at said proximal end for engaging the driver;
    wherein said crest adjacent said proximal end tapers proximally toward said root.

19. The screw according to claim 18 wherein said thread crest has a cutting edge that becomes gradually more blunt toward said proximal end.

20. The screw according to claim 18 wherein said taper of said thread crest extends through said root.

21. A bio-compatible screw for use in bone tissue and adapted to be rotated by a driver, said screw comprising:
    a shank having a longitudinal axis, a distal tip and a proximal end;
    at least one helical thread disposed about said shank for engaging bone tissue, said thread having a crest and a root; and
    driver receiving means at said proximal end for engaging the driver;
    wherein said thread and said proximal end of said shank terminate in a common plane.

22. The screw according to claim 21 wherein said proximal end is radiused.

23. The screw according to claim 1 wherein said threads and said proximal end of said shank terminate in a common plane.

24. The screw according to claim 14 wherein said threads and said proximal end of said shank terminate in a common plane.

25. A method of affixing bone tissue to an object comprising the steps of:
(a) securing a screw to the bone tissue by threadedly engaging the bone tissue with plural interleaved helical threads of the screw;
(b) minimizing net lateral force exerted on said screw during step (a), said step of minimizing comprising providing plural substantially planar tip surfaces at the distal tip of the screw to terminate the plural interleaved threads, respectively; and
wherein entry of the helical threads into the bone tissue during step (a) is effected by the step of (c) cutting into the bone tissue with plural cutting edges corresponding to respective intersections of the plural threads with their planar tip surfaces.

26. The method of claim 25 wherein step (c) includes entering the bone tissue with said cutting edges from plural locations disposed symmetrically about said longitudinal axis.

27. The method of claim 25 wherein said screw is an interference screw and said object is a bone plug disposed in a tunnel in said bone tissue, and wherein step (a) includes simultaneously cutting plural interleaved threads into both said bone plug and a wall of said tunnel with said plural helical threads, respectively.

* * * * *